United States Patent [19]
Aeby et al.

[11] Patent Number: 5,021,066
[45] Date of Patent: Jun. 4, 1991

[54] OXIDATIVE HAIR DYE COMPOSITION BASED ON A GEL VEHICLE AND A PROCESS TO DYE HAIR

[75] Inventors: Johann Aeby, Marly; Herbert Mager, Fribourg, both of Switzerland; Eugen Konrad, Darmstadt, Fed. Rep. of Germany

[73] Assignee: Wella Aktiengesellschaft, Darmstadt, Fed. Rep. of Germany

[21] Appl. No.: 449,078

[22] Filed: Dec. 8, 1989

Related U.S. Application Data

[63] Continuation of Ser. No. 192,516, filed as PCT EP87/00384 on Jul. 15, 1987, published as WO88/00823 on Feb. 11, 1988, abandoned.

[30] Foreign Application Priority Data

Jul. 31, 1986 [DE] Fed. Rep. of Germany ....... 3625916

[51] Int. Cl.$^5$ ............................................... A61K 7/13
[52] U.S. Cl. ........................................... 8/408; 8/405; 8/406; 8/407; 8/410; 8/411; 8/412; 8/416; 8/421; 8/424; 424/70
[58] Field of Search ................... 8/406, 407, 408, 410, 8/411, 412, 416, 421, 424; 424/70

[56] References Cited

U.S. PATENT DOCUMENTS

| 4,169,704 | 10/1979 | Fakhouri | 8/421 |
| 4,171,952 | 10/1979 | Fakhouri | 8/421 |
| 4,348,202 | 9/1982 | Grollier et al. | 8/406 |
| 4,698,065 | 10/1987 | Hoeffkes et al. | 8/406 |
| 4,719,930 | 1/1988 | Gross et al. | 8/406 |

FOREIGN PATENT DOCUMENTS

| 2532174 | 3/1984 | France . |
| 1287343 | 8/1972 | United Kingdom . |
| 2003938 | 3/1979 | United Kingdom . |
| 2065177 | 6/1981 | United Kingdom . |
| 8502999 | 7/1985 | World Int. Prop. O. . |

Primary Examiner—Paul Lieberman
Assistant Examiner—Linda D. Skaling
Attorney, Agent, or Firm—Michael J. Striker

[57] ABSTRACT

A composition for the oxidative dyeing of hair based on a gel vehicle and a dye mixture dissolved therein, wherein the gel vehicle contains
   A) from 12 to 16% by weight of oleic acid,
   B) from 12 to 30% by weight of nonyl phenol, ethoxylated with from 2 to 6 moles of ethylene oxide, and/or of fatty alcohol, having from 12 to 20 carbon atoms, ethoxylated with from 2 to 6 moles of ethylene oxide,
   C) from 8 to 14% by weight of fatty alcohol having from 10 to 20 carbon atoms,
   D) from 4 to 18% by weight of ethanol and/or isopropanol, and
   E) from 16 to 70% by weight of water.

The new composition allows the ammonia it contains to escape more slowly, and it darkens less, when hydrogen peroxide is added, than the known gel hair dye compositions.

16 Claims, No Drawings

OXIDATIVE HAIR DYE COMPOSITION BASED ON A GEL VEHICLE AND A PROCESS TO DYE HAIR

This application is a continuation of application Ser. No. 192,516, filed as PCT EP87/00384 on Jul. 15, 1987, published as WO88/00823 on Feb. 11, 1988, now abandoned.

SPECIFICATION

Gels play an important role as vehicles for hair dyes. They are preferably obtained by using oleic acid in combination with nonyl phenols or fatty alcohols ethoxylated with from 2 to 6 moles of ethylene oxide. Ethanol or isopropanol is typically also contained in the gels, for adjusting the viscosity. The viscosity decreases with increasing alcohol content.

The above-described gels are widely used, because they are very simple and reliable to prepare using inexpensive raw materials, and because as a rule the viscosity obtained is easily reproduced and remains constant over long storage.

Besides the above advantages, however, the conventional gels also have some disadvantages. For instance, the ammonia contained in the hair dye compositions is quickly given off from the gels to the environment, causing an odor problem. A loss of ammonia in the hair dye composition also lessens the covering power of the dyes, especially on gray hair.

The known gels also darken very quickly after being mixed with hydrogen peroxide. Since this darkening ensues faster than the development of the hair dye, the progress of the hair dyeing cannot be observed directly, which may lead the user to draw inaccurate conclusions as to timing and depth of color when dyeing hair.

It is therefore the object of the invention to furnish a new hair dye composition based on a gel vehicle having the above advantages, in which little ammonia is given off and in which less darkening of the vehicle takes place after hydrogen peroxide is added.

It has now been found that the stated object is excellently well attained by means of an oxidative hair dye composition based on a gel vehicle and a dye mixture dissolved therein, characterized in that the gel vehicle contains A) from 8 to 16% by weight of oleic acid,
B) from 8 to 30% by weight of nonyl phenol, ethoxylated with from 2 to 6 moles of ethylene oxide, and/or of fatty alcohol, having from 12 to 20 carbon atoms, ethoxylated with from 2 to 6 moles of ethylene oxide,
C) from 6 to 14% by weight of fatty alcohol having from 10 to 20 carbon atoms,
D) from 4 to 18% by weight of ethanol and/or isopropanol, and
E) from 16 to 70% by weight of water, as a proportion of the total quantity of the hair dye composition.

In the new hair dye composition, the oleic acid is preferably contained in an amount of approximately 10 to 12% by weight; the nonyl phenol ethoxylated with from 2 to 6 moles of ethylene oxide and the fatty alcohol ethoxylated with from 2 to 6 moles of ethylene oxide are preferably contained in an amount of approximately 12 to 25% by weight; the fatty alcohol is preferably contained in an amount of approximately 8 to 12% by weight; the ethanol and the isopropanol are preferably contained in an amount of approximately 6 to 12% by weight; and the water is preferably contained in an amount of from 25 to 50% by weight.

It is not only unexpected but was also unforeseeable that the gel vehicle remains transparent despite the high fatty alcohol content.

Nonyl phenol ethoxylated with 4 moles of ethylene oxide, for example, is an example of a suitable ethoxylated nonyl phenol.

The ethoxylated fatty alcohol of component B) preferably has from 16 to 18 carbon atoms. A suitable ethoxylated fatty alcohol is, for example, lauryl alcohol ethoxylated with 2 moles of ethylene oxide.

Examples of suitable fatty alcohols are cetyl stearyl alcohol, which can also be used in the form of a colloid-dispersed mixture of 90 parts cetyl stearyl alcohol and 10 parts sodium lauryl sulfate, which is sold under the names Lanette$^R$ 0 and Lanette$^R$ W by the Henkel company.

The vehicle can additionally contain still other additives typical for such compositions, such as multivalent alcohols such as ethylene glycol, 1,2-propylene glycol and glycerin, as well as wetting agents or emulsifiers from the classes of anionic, cationic, amphoteric or nonionic surfactants such as fatty alcohol sulfates, ethoxylated fatty alcohol sulfates, alkyl sulfonates, alkyl benzene sulfonates, fatty acid taurides, alkyl trimethylammonium salts, alkyl betaines, fatty acid alkanolamides, ethoxylated fatty acid esters, in addition to conditioners such as lanolin derivatives, cholesterol, pantothenic acid and betaine.

The aforementioned ingredients are used in the amounts typical for such purposes; for example, the wetting agents and emulsifiers can be contained in the preparations in concentrations of approximately 0.5 to 10% by weight and the conditioners in concentrations of approximately 0.1 to 5% by weight.

The vehicle can also contain antioxidants such as ascorbic acid, resorcin or sodium sulfite, as well as up to 0.1% by weight of perfume oils and up to 5.0% by weight of complex formers for heavy metals, in each case as a proportion of the total composition.

Depending on the composition, the hair dye composition according to the invention may be react in a slightly acidic, neutral or alkaline manner. In particular, it has a pH value in the alkaline range between 8.0 and 11.5, the adjustment being effected preferably with approximately 0.1 to 5.0% by weight of ammonia. However, organic amines, such as monoethanolamine and triethanolamine, or inorganic bases, such as sodium hydroxide and potassium hydroxide, can also be used.

The dye mixture contained in the new gel hair dye composition comprises at least one developer substance and at least one coupler substance. Optionally, dye precursors that coupled directly with themselves and dyes that steep directly onto the hair can be used.

The developer and coupler substances are used in the hair dye composition either as such or in the form of their physiologically safe salts with inorganic or organic acids, such as in the form of chloride, sulfate, phosphate or acetate.

Of the known developer substances, 1,4-diaminobenzene, 2,5-diaminotoluene, 2,5-diaminobenzyl alcohol, 2-(2'-hydroxyethyl)-1,4-diaminobenzene and 4-aminophenol are possible as ingredients of the new hair dye composition.

As the suitable coupler substance, the following examples can be given: resorcin, 4-chlororesorcin, 2,4-dichlororesorcin, 2-methylresorcin, 3-aminophenol, 5-amino-2-methylphenol, 4-amino1,2-methylenedioxybenzene, 4-(2'-hydroxyethyl)amino-1,2-methylenedioxybenzene, 4-(2'-hydroxyethyl)amiono-1,2-methylenedioxybenzene, 1-naphthol, 4 hydroxyindole, 2,4-dihydroxyanisole, 3-aminoaniline, 2-amino-4-(2-hydroxyethyl)aminoanisole and 2', 4'-dihydroxy-2-phenoxyethanol.

The total amount of the developer-substance and coupler-substance combination contained in the hair dye composition described here should be approximately 0.1 to 6.0% by weight, preferably approximately 0.5 to 5.0% by weight.

To attain certain shades, conventional direct-steeping dyes can also be contained, for example aromatic nitro dyes such as 2-amino-4-nitrophenol, 2-amino-6-chloro-4-nitrophenol, 2-(2'-hydroxyethyl)amiono-4,6-dinnitrophenol, 3-(2',3'-dihydroxypropyl)-amino-4-nitrotrifluoromethylbenzene, and Disperse Violet 1 (C. I. 61,100) and 1,4,5,8-tetraaminoanthraquinone.

The total amount of the dye mixture is approximately from 0.1 to 6.0% by weight, preferably approximately 0.5 to 5.0% by weight.

The oxidative hair dye composition according to the invention is a mixture of the gel vehicle and the dye mixture.

For use, the hair dye composition is mixed immediately prior to use in a proportion by weight of approximately 5:1 to 1:4 with an oxidant, and an amount of this mixture sufficient for the dye treatment and depending on the fullness of the hair, generally approximately 60 to 200 g, is applied to the hair. A primary example of an oxidant for developing the hair color is hydrogen peroxide, for example as a 6% aqueous solution, or its addition compounds with urea, melamine or sodium borate. The mixture is allowed to act on the hair for approximately 10 to 45 minutes, preferably 30 minutes, at 15 to 50° C.; the dye mixture is then rinsed with water and the hair is dried. Optionally, this rinsing is followed by rinsing with a weak physiologically safe organic acid, such as citric acid or tartaric acid.

The hydrogen peroxide used in combination with the new oxidative hair dye composition can be in the form of either an aqueous solution or an emulsion of low to medium viscosity. As a rule, hydrogen peroxide in the emulsion form is used, if the hair dye composition is applied to the hair with an applicator brush. In the event that the hair dyeing is performed with an applicator bottle, then the use of hydrogen peroxide in an aqueous solution is preferred. In that case the hydrogen peroxide is first placed in the applicator bottle. Then the hair dye composition is forced out of the tube into the hydrogen peroxide solution, and then the applicator bottle is shaken to mix the oxidative dye composition so that it is ready for use. The mixing process is fast and unproblematic. The finished oxidative dye composition can then be dispensed by squeezing on the applicator bottle slightly.

To thicken the hydrogen peroxide used in emulsion form, approximately 1 to 2% by weight of cetyl stearyl alcohol in combination with anionic emulsifiers, such as lauryl alcohol diglycolether sulfate, can be used.

The hair dye compositions according to the invention have, the advantageous propoerty of not thickening even after long storage, which would make them less miscible with the hydrogen peroxide.

The new hair dye compositions characterized by the gel vehicle according to the invention have the same viscosity, largely independently of the type and amount of dyes they contain. It is therefore possible to use the same vehicle for all shades in one hair dye series, thus not only making it easier for the user to handle the hair dye composition by the user but making production simpler and hence less expensive.

EXAMPLES OF HAIR DYE COMPOSITIONS

EXAMPLE 1

Oxidative Hair Dye Composition in Gel Form

| | |
|---|---|
| 12.0 g | oleic acid, distilled |
| 25.0 g | nonyl phenol, ethoxylated with 4 moles of ethylene oxide |
| 10.0 g | cetyl stearyl alcohol |
| 8.0 g | isopropanol |
| 1.0 g | 1,4-diaminobenzene |
| 0.8 g | resorcin |
| 0.1 g | 3-aminophenol |
| 0.1 g | 4-aminophenol |
| 0.3 g | ascorbic acid |
| 10.0 g | ammonia, 25% aqueous solution |
| 32.7 g | water |
| 100.0 g | |

The above hair dye composition is mixed in a proportion by weight of 1:2 with an aqueous 6% solution of hydrogen peroxide in an applicator bottle by shaking, and the resultant hair dye solution is applied to belached or gray hair. By the end of an action period of 20 minutes at 40° C., the hair has been dyed medium blond.

EXAMPLE 2

Oxidative Hair Dye Composition in Gel Form

| | |
|---|---|
| 10.0 g | oleic acid, distilled |
| 12.0 g | lauryl alcohol, ethoxylated with 2 moles of ethylene oxide |
| 10.0 g | cetyl stearyl alcohol |
| 8.0 g | isopropanol |
| 0.1 g | sodium sulfite |
| 0.3 g | ascorbic acid |
| 3.0 g | lauryl alcohol diglycolether sulfate sodium salt, 28% aqueous solution |
| 2.0 g | 1,4-diaminobenzene |
| 0.4 g | 3-aminophenol |
| 1.6 g | resorcin |
| 9.0 g | ammonia, 25% aqueous solution |
| 43.6 g | water |
| 100.0 g | |

The above hair dye composition is mixed in a proportion by weight of 1:1 with an emulsion comprising

| | |
|---|---|
| 1.0 g | cetyl stearyl alcohol |
| 0.3 g | lauryl alcohol diglycolethersulfate sodium salt, 28% aqueous solution |
| 98.7 g | hydrogen peroxide, 6% aqueous solution |
| 100.0 g | | and the resultant viscous hair dye composition is applied to gray hair with a brush. By the end of an action period of 20 minutes at 40° C., the hair has been dyed dark brown.

The percentages given in this application represent percentages by weight, unless otherwise noted.

What is claimed is:

1. A composition for oxidative dyeing of hair consisting of a gel vehicle and a dye mixture dissolved therein, wherein the gel vehicle consists of
   A) from 8 to 16% by weight of oleic acid,
   B) from 12 to 30% by weight of an ethoxylated alcohol selected from the group consisting of nonyl phenol ethoxylated with from 2 to 6 moles of ethylene oxide, fatty alcohols having 12 to 20 carbon atoms ethoxylated with from 2 to 6 moles of ethylene oxide and mixtures thereof, C) from 8 to 14% by weight of a fatty alcohol having from 10 to 20 carbon atoms, D) from 4 to 18% by weight of an alcohol selected from the group consisting of ethanol, isopropanol and mixtures thereof, E) from 0 to 0.5% by weight of antioxidants, F) from 0 to 0.1% by weight of perfume oils, G) from 0 to 5.0% by weight of complexing agents, H) from 0.1 to 10% by weight of wetting agents and emulsifiers, I) from 0.1 to 5.0% by weight conditioners selected from the group consisting of lanolin derivatives, cholesterol, pantothenic acid, and betaine J) from 0.1 to 5% by weight of an organic or inorganic base selected from the group consisting of ammonia, monoethanolamine, triethanolamine, sodium hydroxide and potassium hydroxide, K) from 16 to 70% by weight of water, as a proportion of the total quantity of the hair dye composition, wherein the sum total of the % by weight of said components A) to K) does not exceed 99.9 %.

2. A composition as defined by claim 1, containing from approximately 10 to 12% by weight of said oleic acid.

3. A composition as defined by claim 1, containing from approximately 16 to 25% by weight of said ethoxylated alcohol.

4. A composition as defined by claim 1, containing from approximately 8 to 12 % by weight of said fatty alcohol.

5. A composition as defined by claim 1, containing from approximately 6 to 12 % of said alchol selected from the group consisting of ethanol, isopropanol and a mixture thereof.

6. A composition as defined by claim 1, wherein said ethoxylated alcohol is selected from the group consisting of nonyl phenol ethoxylated from the group consisting of nonyl phenol ethoxylated with 4 moles of ethylene oxide, a fatty alcohol ethoxylated with 4 moles of ethylene oxide containing 12 to 20 carbon atoms and a mixture thereof.

7. A composition as defined by claim 6, wherein said fatty alcohol ethoxylated with said 4 moles of ethylene oxide contains 16 to 18 carbon atoms.

8. A composition as defined by claim 1, wherein said dye mixture dissolved is said gel vehicle contains at least one of the following developer substances: 4-aminophenol, 1,4-diaminobenzene, 2,5-diaminotoluene, 2,5-diaminobenzyl alcohol, 3-methyl-4-aminophenol and 2-(2'-hydroxyethyl)-1,4-diaminobenzene.

9. A composition as defined by claim 7, wherein said dye mixture dissolved in said gel vehicle contains at least one of the following coupler substances: 4-chlororesorcin, 2-methylresorcin, 3-amionophenol, 5-amiono-2-methylphenol, 4-amiono-1,2-methylenedioxybenzene, 4-(2'-hydroxyethyl)amino-1,2-methylenedioxybenzene, 1-naphthol, 3-aminoaniline and 2-amiono-4-(2'-hydroxyethyl)aminoanisol.

10. A composition as defined by claim 8, wherein said dye mixture dissolved in said gel vehicle further contains at least one coupler substance, the sum total amount of said developer substance and said coupler substance being from 0.1 to 6.0% by weight.

11. A composition as defined by claim 9, wherein said dye mixture dissolved in said gel vehicle further contains at least one developer substance, the sum total amount of said developer substance and said coupler substance being from 0.1 to 6.0% by weight.

12. A composition as defined by claim 2, containing from 16 to 25% by weight of said ethoxylated alcohol.

13. A composition as defined by claim 1, wherein said fatty alcohol has from 14 to 20 carbon atoms.

14. A method for oxidative dyeing of hair which comprises the steps of:
   a) providing an oxidative hair dye composition according to claim 1;
   b) treating the oxidative hair dye composition defined in step a) with an oxidant immediately prior to use;
   c) applying an amount of the oxidative hair dye composition during step b) sufficient for hair dye treatment to the hair to be dyed;
   d) allowing the oxidative hair dye composition to act on the hair for approximately 10 to 45 minutes at 15° to 50° C.; and
   e) rinsing the hair with water and dyeing the hair.

15. The method for oxidative dyeing of hair defined in claim 14, wherein said oxidant of step b) is a member selected from the group consisting of hydrogen peroxide, a hydrogen peroxide addition compound with urea, a hydroxgen peroxide addition compound with melamine and a hydrogen peroxide addition compound with sodium borate.

16. The method for oxidative dyeing of hair defined in claim 14, wherein said oxidative hair dye composition and said oxidant are in a ratio of from 5:1 to 1:4 in step b).

* * * * *